US010456596B2

(12) United States Patent
Umezawa et al.

(10) Patent No.: US 10,456,596 B2
(45) Date of Patent: Oct. 29, 2019

(54) PARTICLE THERAPY SYSTEM

(71) Applicant: HITACHI, LTD., Tokyo (JP)

(72) Inventors: Masumi Umezawa, Tokyo (JP);
Shinichiro Fujitaka, Tokyo (JP);
Taisuke Takayanagi, Tokyo (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 15/775,197

(22) PCT Filed: Nov. 13, 2015

(86) PCT No.: PCT/JP2015/082046
§ 371 (c)(1),
(2) Date: May 10, 2018

(87) PCT Pub. No.: WO2017/081826
PCT Pub. Date: May 18, 2017

(65) Prior Publication Data
US 2018/0326224 A1    Nov. 15, 2018

(51) Int. Cl.
*A61N 5/10*   (2006.01)
*G21K 1/02*   (2006.01)

(52) U.S. Cl.
CPC .......... *A61N 5/1043* (2013.01); *A61N 5/1071* (2013.01); *A61N 2005/1072* (2013.01);
(Continued)

(58) Field of Classification Search
CPC ...... A61N 5/10; A61N 5/1043; A61N 5/1071; A61N 2005/1072; A61N 2005/1074; A61N 2005/1087; G21K 1/025
See application file for complete search history.

(56) References Cited

U.S. PATENT DOCUMENTS

2009/0296885 A1* 12/2009 Boeh .................. A61N 5/1042
378/65
2010/0074408 A1   3/2010 Bert et al.
(Continued)

FOREIGN PATENT DOCUMENTS

EP    2 489 406 A1    8/2012
JP    2009-066106 A   4/2009
(Continued)

OTHER PUBLICATIONS

International Search Report of PCT/JP2015/082046 dated Dec. 15, 2015.
(Continued)

*Primary Examiner* — David E Smith
(74) *Attorney, Agent, or Firm* — Mattingly & Malur, PC

(57) ABSTRACT

The invention provides a particle therapy system in which whether to perform any one irradiation method of a raster scanning method and a discrete spot scanning method can also be selected based on previous selection depending on a target volume 41 of a patient 4 to be irradiated, and either of the irradiation methods of the raster scanning method and the discrete spot scanning method is configured to be capable of being performed by one irradiation apparatus 500. Therefore, a small particle therapy system capable of achieving both higher accuracy irradiation and high dose rate improvement is provided.

10 Claims, 7 Drawing Sheets

(52) U.S. Cl.
CPC ............... *A61N 2005/1074* (2013.01); *A61N 2005/1087* (2013.01); *G21K 1/025* (2013.01)

(56) References Cited

U.S. PATENT DOCUMENTS

| | | | | |
|---|---|---|---|---|
| 2012/0305790 | A1* | 12/2012 | Hanawa | A61N 5/1043 |
| | | | | 250/393 |
| 2013/0324785 | A1* | 12/2013 | Bertram | G06F 19/3481 |
| | | | | 600/1 |
| 2014/0018603 | A1* | 1/2014 | Asaba | A61N 5/1031 |
| | | | | 600/1 |
| 2014/0094643 | A1* | 4/2014 | Gall | H05H 13/02 |
| | | | | 600/2 |
| 2015/0131780 | A1* | 5/2015 | Tsunoo | A61N 5/1049 |
| | | | | 378/62 |
| 2015/0306424 | A1* | 10/2015 | Bert | A61N 5/1037 |
| | | | | 600/1 |
| 2017/0173365 | A1* | 6/2017 | Bzdusek | A61N 5/103 |

FOREIGN PATENT DOCUMENTS

| | | |
|---|---|---|
| JP | 2011-161055 A | 8/2011 |
| WO | 2015/083035 A1 | 6/2015 |

OTHER PUBLICATIONS

Extended European Search Report received in corresponding European Application No. 15908343.5 dated Apr. 5, 2019.

\* cited by examiner

[FIG. 1]
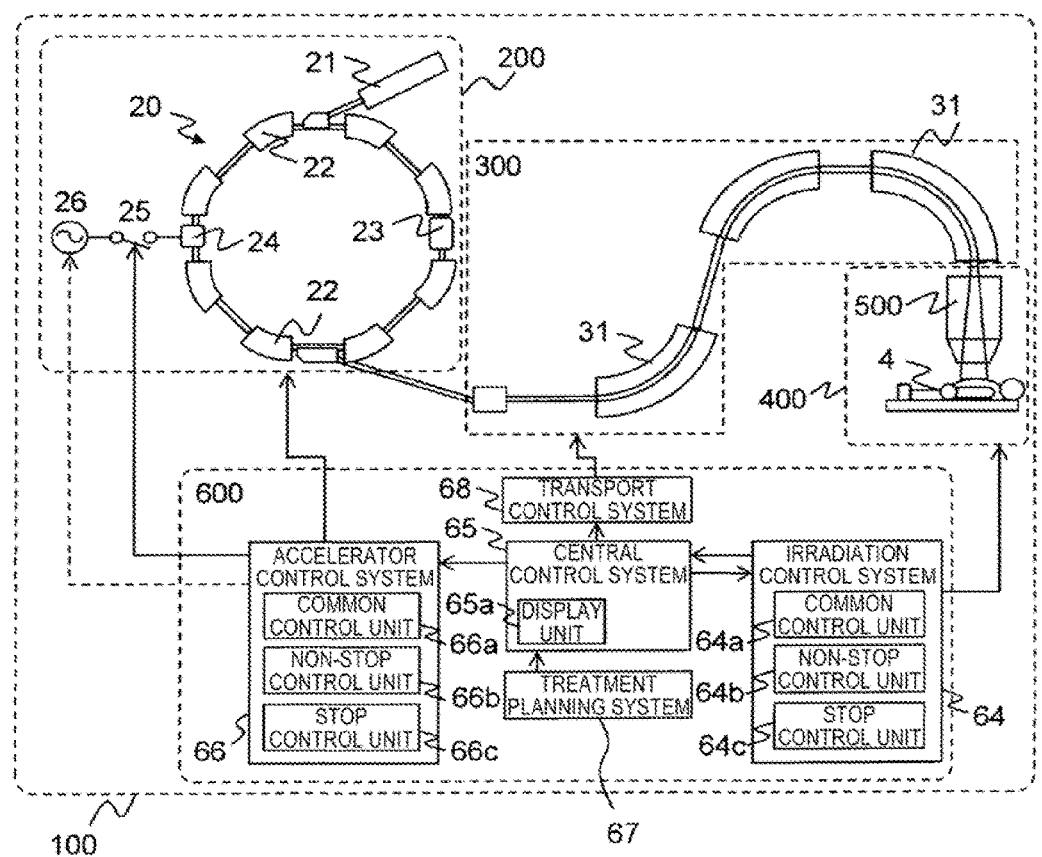

[FIG. 2]
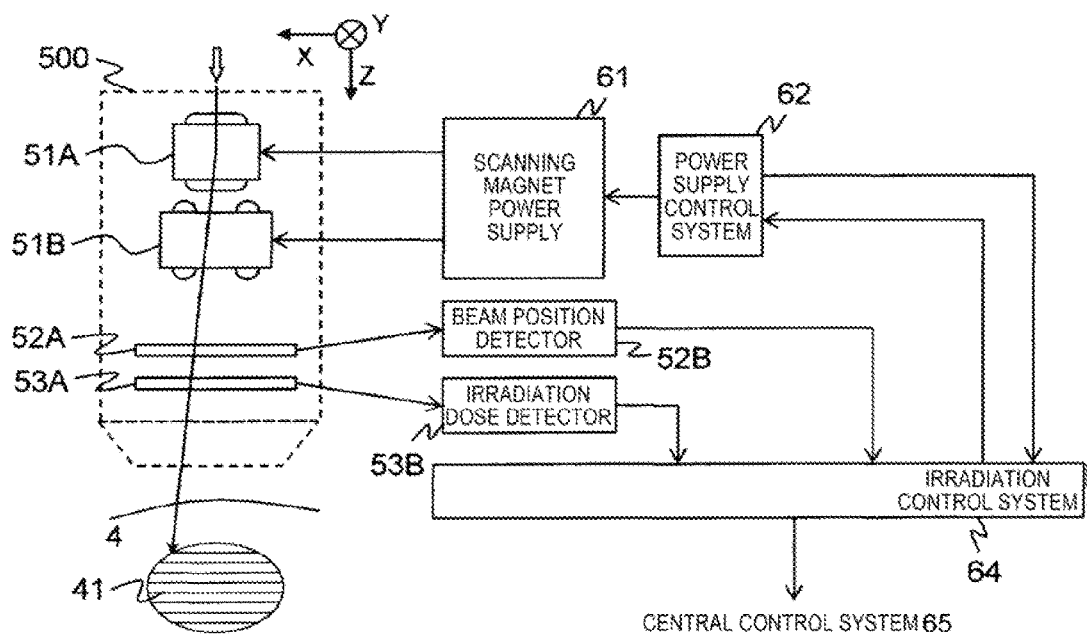
[FIG. 3]
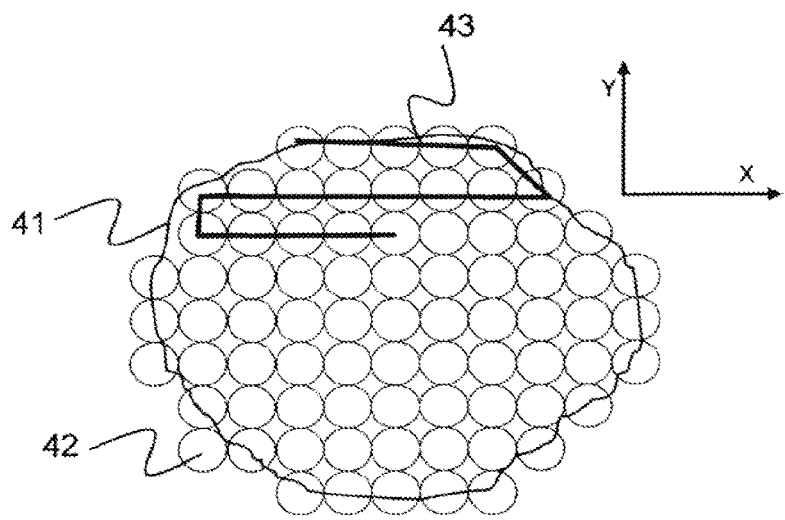

[FIG. 4]
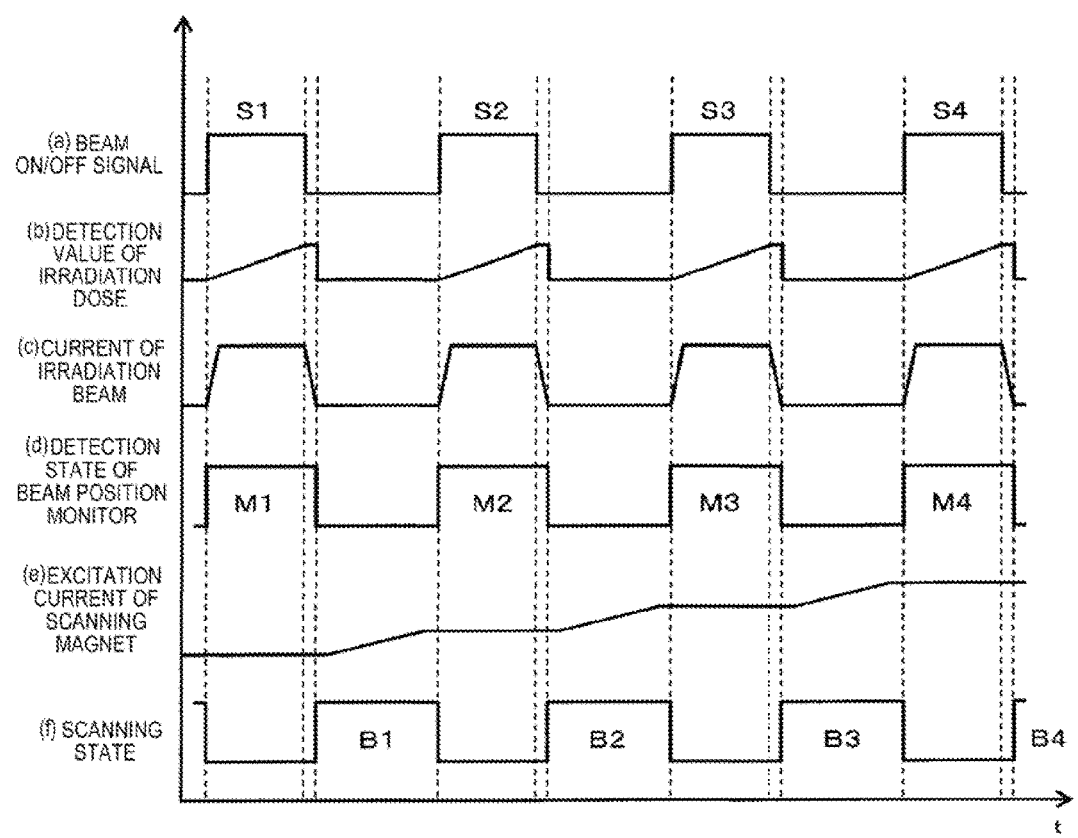

[FIG. 5]
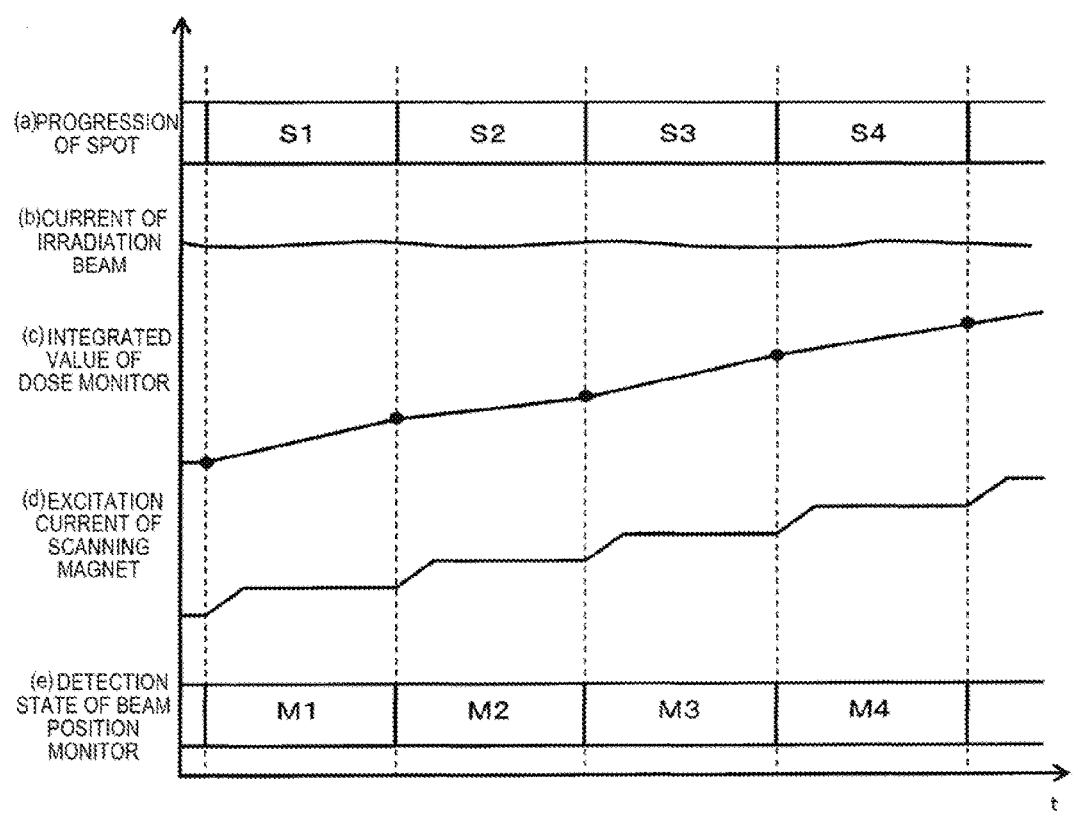

[FIG. 6]
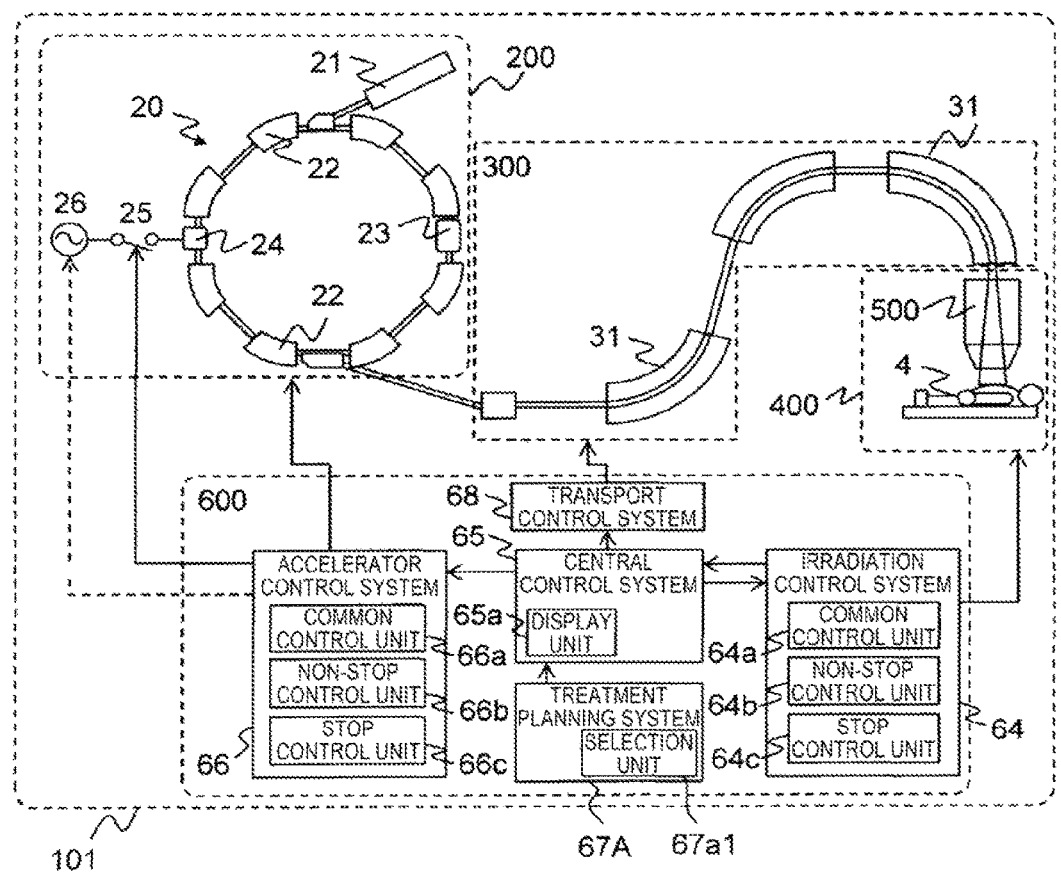

[FIG. 7]
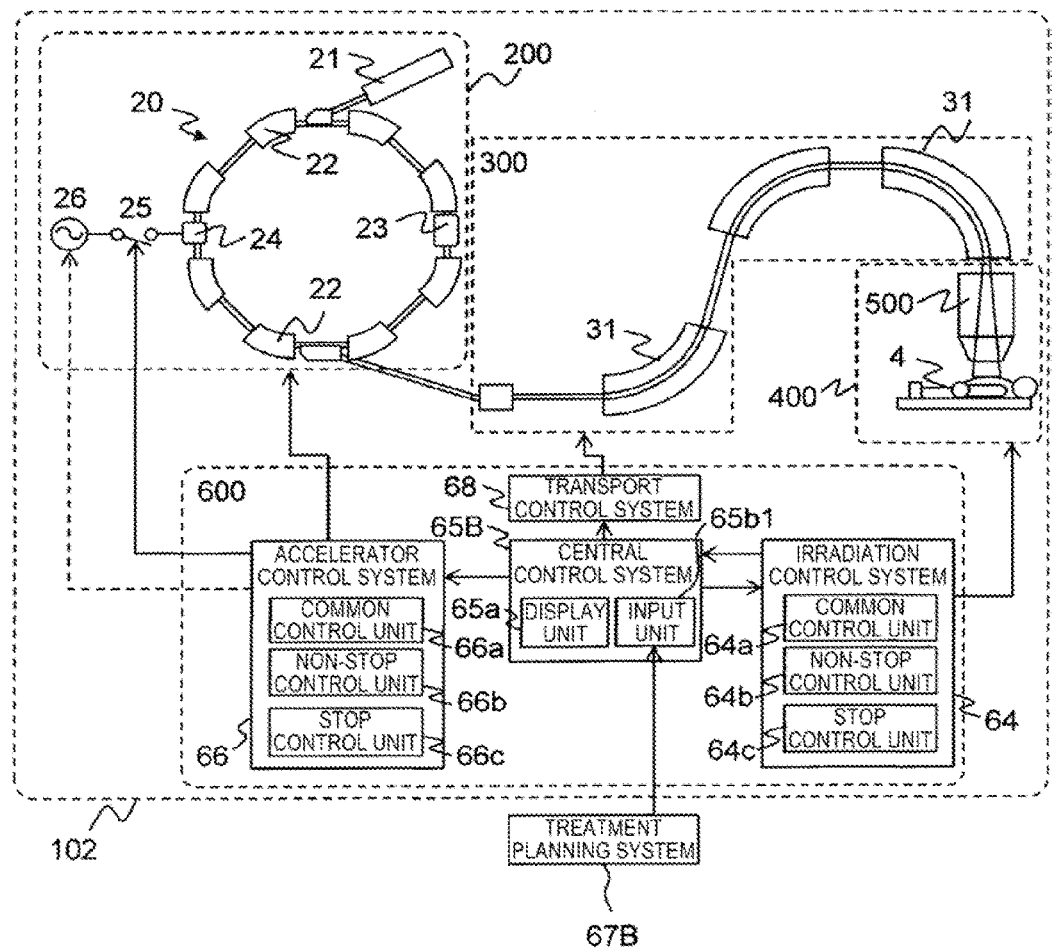

[FIG. 8]
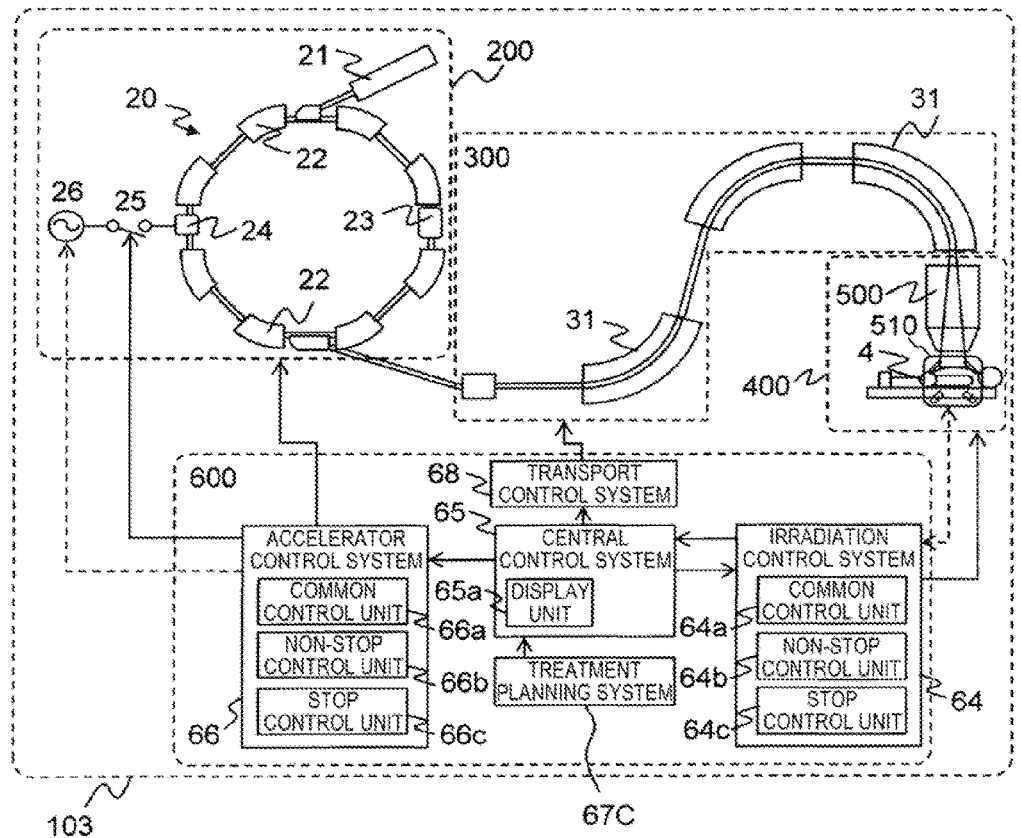
[FIG. 9]
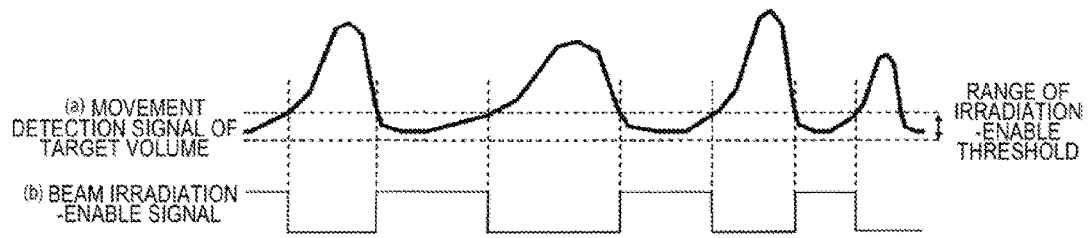

PARTICLE THERAPY SYSTEM

TECHNICAL FIELD

The present invention relates to a particle therapy system.

BACKGROUND ART

A particle beam irradiation apparatus making an actual dose distribution consistent to a planned dose distribution to provide the inside of a target volume with a uniform dose distribution is disclosed in JP-A-2009-66106 (PTL 1) which is characterized by including: a beam generation unit for generating particle beams; a beam extraction control unit for controlling extraction of the particle beams; abeam scan command unit sequentially and two-dimensionally commanding positions of the particle beams to scan slices, which are formed by dividing the target volume to be irradiated along an axial direction of the particle beams, along predetermined trace patterns set in the slices; and a beam scan unit for two-directionally scanning the slices with the particle beams based on the command signal from the beam scan command unit, wherein, after scanning the trace pattern along a forward direction, the beam scan command unit commands the scan positions for scanning the trace patterns along an inverse direction.

CITATION LIST

Patent Literature

PTL 1: JP-A-2009-66106

SUMMARY OF INVENTION

Technical Problem

There is known a therapy method of irradiating a patient's target volume such as cancer with any particle beams (an ion beam; hereinafter referred to as an ion beam) such as protons or carbon ions. A particle beam irradiation system used in such a therapy includes an ion beam generator, a beam transport system, and an irradiation apparatus.

As an irradiation method of the irradiation apparatus, a scatterer method of cutting a beam shape with a collimator in conformity with a target shape after spreading a beam with a scatterer or a beam scanning method of scanning a thin beam in a target volume region is known.

In the particle beam irradiation system using the beam scanning method, an ion beam accelerated by an accelerator of the ion beam generator reaches to the irradiation apparatus via the beam transport system, is scanned onto a plane vertical to a beam traveling direction by a scanning magnet provided in the irradiation apparatus, and is irradiated onto the target volume of the patient from the irradiation apparatus.

As a method of forming a uniform radiation field distribution in the beam scanning method, a wobbler method is known in which the thin beam is appropriately scattered and then scanned in a circular shape, a spiral shape, or a zigzag shape. In this case, it is necessary to cut out the formed uniform distribution with the collimator in conformity with the target shape.

On the other hand, a spot scanning method is known as a method of making the dose distribution applied with the thin beam conformal to the target shape or forming an arbitrary dose distribution rather than uniform. This is to divide the target shape into minute small regions (irradiation spots) and to set and irradiate a desired irradiation dose for each section in advance.

The spot scanning method includes two irradiation methods that are generally classified into a discrete spot scanning method and a raster scanning method, and the flow of processing with respect to the respective methods is disclosed in PTL 1. As defined in PTL 1, the discrete spot scanning method is a method in which extraction of the beam is stopped while moving a position of the particle beam to the next irradiation spot from any irradiation spot and the extraction of the beam is restarted after completion of the movement, and the raster scanning method is a method in which the extraction of the beam is continued without interruption while scanning the same slice. In the two particle therapy systems each implementing these two spot scanning method, performance and control contents of the instrument are different depending on instrument specifications of the accelerator, extraction control of the accelerator, and beam monitoring which are required. In addition, these two spot scanning methods can be substituted for each other, and there is no suggestion of the need to use properly.

However, as a general need of the particle therapy system, there is a demand to aim at a further highly accurate irradiation and there is also a demand for a high dose rate to increase the number of treatable patients. In response to such a problem, the present inventors have found the following viewpoints.

The discrete spot scanning method and the raster scanning method cause benefits in different cases. In particular, the discrete spot scanning method enables highly accurate irradiation in moving object tracking. Since the X-ray irradiation for tracking the target volume necessary for movement of the target volume is performed between spots where the particle beam is not irradiated, it is advantageous in terms of dose management accuracy and target volume identification accuracy. On the other hand, the raster scanning method is advantageous in throughput because the irradiation period of continuous irradiation is relatively long, and is advantageous in the case of organs with less movement and keeping on periodically for a fixed time.

However, in a system which adopts a plurality of nozzles implementing different spot scanning methods or a system having a plurality of treatment rooms implementing different irradiation methods, there is a problem of handling the nozzles in the treatment room and space. Particularly, in hospitals located in urban areas with many patients, it is not desirable to easily increase the footprint size and the number of treatment rooms of the particle therapy system.

The present invention has been made in view of such circumstances, and an object thereof is to provide a small particle therapy system capable of achieving both higher accuracy irradiation and high dose rate improvement.

Solution to Problem

In order to solve the above problems, for example, the configuration described in claims is adopted.

The present invention includes a plurality of units for solving the above problems, but as an example is characterized by a particle therapy system that divides an irradiation object into a plurality of small regions and sequentially irradiates the plurality of small regions with a particle beam, the particle therapy system including: an accelerator that accelerates the particle beam; an irradiation apparatus that irradiates a target with the particle beam accelerated by the accelerator; and a control system that controls the accelerator and the irradiation apparatus, wherein the accelerator, the irradiation apparatus, and the control system are capable of performing, with the irradiation apparatus, both irradiation methods of an irradiation method in which irradiation of the particle beam is not stopped when moving to the next small region and an irradiation method in which irradiation of the particle beam is stopped.

Advantageous Effects of Invention

According to the present invention, both higher accuracy irradiation and high dose rate improvement of the particle beam irradiation can be achieved.

BRIEF DESCRIPTION OF DRAWINGS

FIG. 1 is a diagram illustrating schematically an overall configuration of a particle therapy system according to a preferred embodiment (first embodiment) of the present invention.

FIG. 2 is a diagram illustrating a configuration of an irradiation apparatus used in the particle therapy system according to the first embodiment.

FIG. 3 is a diagram illustrating a specific layer in a depth direction of a target volume to be irradiated.

FIG. 4 is a timing chart illustrating an operation in a case where a discrete spot scanning method is applied by the particle therapy system according to the first embodiment.

FIG. 5 is a timing chart illustrating an operation in a case where a raster scanning method is applied by the particle therapy system according to the first embodiment.

FIG. 6 is a diagram illustrating schematically an overall configuration of a particle therapy system according to a second embodiment.

FIG. 7 is a diagram illustrating schematically an overall configuration of a particle therapy system according to a third embodiment.

FIG. 8 is a diagram illustrating schematically an overall configuration of a particle therapy system according to a fourth embodiment.

FIG. 9 is a diagram illustrating a relation between a target volume movement detection signal and a beam irradiation enable signal in the particle therapy system according to the fourth embodiment.

DESCRIPTION OF EMBODIMENTS

Embodiments of particle therapy systems according to the present invention will be described below with reference to the drawings.

First Embodiment

A particle therapy system according to a first embodiment of the present invention will be described with reference to FIGS. 1 to 5.

First, an overall configuration will be described with reference to FIG. 1. FIG. 1 is a schematic diagram illustrating the overall configuration of the particle therapy system according to the first embodiment.

A particle therapy system 100 includes an ion beam generator 200, a beam transport system 300 that guides a generated ion beam to a treatment room 400, an irradiation apparatus 500 that irradiates a target volume 41 (illustrated in FIG. 2) of a patient 4 in conformity with the shape thereof with the ion beam in the treatment room 400, and a control system 600.

The ion beam generator 200 includes a preaccelerator 21 and a synchrotron 20 that accelerates a charged particle pre-accelerated by the preaccelerator 21 up to a predetermined energy level and then extracts the charged particle. Instead of the synchrotron 20, an accelerator such as a cyclotron or a linear accelerator not having a preaccelerator may be used.

The synchrotron 20 is an apparatus for accelerating ion beams (protons, heavy particle ions such as carbon, neutrons, or the like) accelerated by the preaccelerator 21 to a predetermined energy level, and includes a plurality of bending magnets 22 and a plurality of quadrupole magnets (not illustrated) that circulate the ion beam, a radiofrequency acceleration system 23 that accelerates the circulating ion beam, and an extraction apparatus 24 that extracts the ion beam accelerated to the predetermined energy level.

The extraction apparatus 24 includes an extraction radiofrequency electrode (not illustrated) for extraction, the extraction radiofrequency electrode is connected to a radiofrequency power supply 26 via an extraction switch 25, and ON/OFF of extraction of the ion beam is performed by opening/closing of the extraction switch 25.

The beam transport system 300 includes a plurality of bending magnets 31 and a plurality of quadrupole magnets (not illustrated), and is configured to transport the ion beam extracted from the synchrotron 20 to the irradiation apparatus 500.

Here, a configuration of the irradiation apparatus 500 used in the particle therapy system. 100 according to the present embodiment will be described with reference to FIG. 2. FIG. 2 is a diagram illustrating the configuration of the irradiation apparatus 500.

The irradiation apparatus 500 includes an X-direction scanning magnet 51A that scans the ion beam accelerated by the synchrotron 20 and guided by the beam transport system 300 in a horizontal direction (an X-direction in the drawing) and makes it conformal to the shape of the target volume 41 of the patient 4 and a Y-direction scanning magnet 51B that scans the ion beam in a vertical direction (a Y-direction in the drawing, which is a direction perpendicular to the page). These scanning magnets 51A and 51B are connected to a scanning magnet power supply 61. The scanning magnet power supply 61 is controlled by a power supply control system 62. The ion beam deflected scanning magnets 51A and 51B passes through a beam position monitor 52A and a dose monitor 53A, and is irradiated to the target volume 41 as an irradiation object. The beam position monitor 52A is connected to a beam position detector 52B, and the beam position detector 52B detects position and width (spread) of the ion beam. The dose monitor 53A is connected to an irradiation dose detector 53B, and the irradiation dose detector 53B detects the amount of the ion beam to be irradiated.

Here, a spot scanning method will be described with reference to FIGS. 2 and 3. FIG. 3 is an explanatory view of the target volume 41 viewed from an upstream side of the ion beam.

As illustrated in FIG. 2, the target shape of the target volume 41 of the patient 4 is three-dimensionally divided into a plurality of layers in a depth direction (a Z-direction in the drawing). As illustrated in FIG. 3, each of the layers is further two-dimensionally divided into in the horizontal direction (the X-Y direction in the drawing) which is a direction crossing the traveling direction of the ion beam to set a plurality of dose sections (small regions, which are described bellow as irradiation spots 42). The depth direction corresponds to an arrival degree of the ion beam, and is changed by an energy change of the ion beam extracted from the synchrotron 20 or an energy change of the ion beam due to the insertion of an energy absorber upstream from the irradiation apparatus 500, whereby each of the layers is selectively irradiated. In each of the layers, the ion beam is two-dimensionally scanned by the scanning magnets 51A and 51B, for example, along a path 43 illustrated in FIG. 3, and thus a predetermined dose is given to each of the irradiation spots 42. The amount of the ion beam irradiated to each of the irradiation spots 42 is detected by the dose monitor 53A and the irradiation dose detector 53B, and the position or the spread (width) of the ion beam is detected by the beam position monitor 52A and the beam position detector 52B.

The irradiation control using the spot scanning method is performed by an irradiation control system 64 for controlling the beam extraction from the ion beam generator 200.

Here, the spot scanning method is generally classified into a discrete spot scanning method which is an irradiation method in which irradiation of the ion beam is stopped when moving to the next irradiation spot 42 and a raster scanning method in which irradiation of the ion beam is not stopped even when moving to the next irradiation spot 42 after the ion beam is irradiated to each of the irradiation spots 42 with a target dose.

In the discrete spot scanning method, since the beam extraction is stopped while the irradiation point of the ion beam is moved from a certain lattice point to the next lattice point and the beam extraction is restarted after the movement is completed, the beam extraction is intermittent while the same slice is scanned.

Therefore, the irradiation control system 64 controls an excitation current of the scanning magnets 51A and 51B to scan the ion beam and changes the irradiation point to the next irradiation spot 42 when the irradiation dose of the ion beam irradiated to one spot 42 of the plurality of irradiation spots 42 reaches to the target dose. Then, the irradiation control system 64 stops the extraction of the ion beam from the ion beam generator 200 when the irradiation does of the ion beam irradiated to one spot reaches the target dose. In the stop state of the beam extraction, the irradiation control system controls the excitation current of the scanning magnets 51A and 51B to scan the ion beam, changes the irradiation point to the next irradiation spot 42, and controls to start the extraction of the ion beam from ion beam generator 200 after the change.

The operation of the discrete spot scanning method will be described in more detail below with reference to FIG. 4. A time chart illustrated in FIG. 4 shows the operation while a certain layer in the target volume 41 illustrated in FIG. 3 is irradiated.

In FIG. 4, a horizontal axis indicates a time t. A vertical axis in FIG. 4(*a*) represents an opening/closing signal output from the irradiation control system 64 to the extraction switch 25 via a central control system 65 and an accelerator control system 66, that is, a beam ON/OFF signal for controlling the extraction of the ion beam. Since there are four ON states, that is, four irradiation spots 42 in FIG. 4(*a*), these spots are defined as S1, S2, S3, and S4, respectively. Here, the initial beam ON signal is generated at a time when preparation for operation of the whole system including the ion beam generator 200 is completed through processes such as beam injection, acceleration of the synchrotron 20 and the ion beam becomes ready for irradiation after a doctor or a therapist instructs the start of irradiation.

A vertical axis of FIG. 4 (*b*) represents an irradiation dose of the irradiate ion beam detected by the dose monitor 53A and the irradiation dose detector 53B, the irradiation dose is integrated at the same time as the beam ON, and the detection signal is taken into the irradiation control system 64. When the integrated dose reaches a predetermined amount, the irradiation control system 64 executes the beam OFF and stores the detected amount in a memory of the irradiation control system 64, and then the irradiation dose detector 53B is reset. Although the irradiation dose detected by the dose monitor 53A and the irradiation dose detector 53B is illustrated herein to be reset for each irradiation spot 42, the irradiation dose may be determined by the difference between values obtained through integration.

FIG. 4(*c*) illustrates an actual irradiation current of the ion beam, and illustrates a case where a minute amount of ion beam is irradiated because there is an OFF reaction time even after the beam reaches a predetermined dose and is turned OFF as illustrated in FIG. 4(*b*). In the discrete spot scanning method, since a leakage current is generated for each irradiation spot due to a transient response after the beam OFF, unless the extraction control of the accelerator and extraction ON/OFF response performance determined by the accelerator are high, a large influence is exerted on uniform dose application.

A vertical axis in FIG. 4(*d*) represents a detection state of the beam position monitor 52A and the beam position detector 52B for detecting position and width of the irradiation beam illustrated in FIG. 4(*c*), and for example, the detection of an irradiation spot S1, that is, a signal collection at a section of M1 is performed by the irradiation control system 64. After completion of the signal collection of the beam position detector illustrated in FIG. 4(*d*), the irradiation control system 64 calculates the beam position a width (standard deviation) based on the collected signal and compares with a tolerance set previously in the memory of irradiation control system 64, thereby determining whether the beam position/width value is within a desired error range.

When the calculation result of the beam position/width deviates from the tolerance, the irradiation control system 64 generates an interlock signal, and stops the progression to the next irradiation spot 42. For example, when the calculation result of the beam position/width of the section S1 at the irradiation spot 42 deviates from the tolerance, the progression stops at an arbitrary timing before a predetermined time in the next section S2. In the discrete spot scanning method, the irradiation beam current flows only during the irradiation period on the irradiation spot and the subsequent response period, the period of monitor detection is also performed therebetween, and the irradiation beam current can be stopped with a delay in a period during which irradiation is not performed between the irradiation spots.

A vertical axis in FIG. 4(*e*) represents a current pattern of the scanning magnet power supply 61 in the case of two-dimensionally scanning the charged particles as illustrated in FIG. 3. Such a pattern is a pattern prescribed in the irradiation control system 64, and indicates an operation of successively changing an excitation amount after the irradiation dose at each irradiation spot 42 reaches the prescribed value and then the irradiation beam stops and changing an irradiation point.

A vertical axis in FIG. 4(*f*) represents a state of the scanning magnet power supply 61, the scanning magnet power supply 61 is turned ON (hereinafter, referred to as a scanning state being ON) while a current deviation deviates from a desired range by a change of the excitation current, and the scanning magnet power supply 61 is turned OFF (hereinafter, referred to as a scanning state being OFF) after the change of the excitation current is completed and it is determined that the current deviation has fallen within the desired range. That is, after the ion beam is irradiated at the section S1 in the irradiation spot 42, the irradiation point is changed to the next irradiation spot 42 in the section B1.

In FIG. 4, the irradiation start at the section S2 in the irradiation spot 42 is the timing at which the irradiation point is changed after the irradiation at the section S1 in the irradiation spot 42, that is, the scanning state being ON in FIG. 4(f) is completed. The flow after the completion at the section S1 in the irradiation spot 42 is also repeated after the irradiation at the section S2 in the irradiation spot 42, and two-dimensional scanning as illustrated in FIG. 3 proceeds.

The series of operations illustrated in FIGS. 4(a) to (f) are repeated, and the layer in the depth direction of the target volume 41 illustrated in FIG. 3 is irradiated with the ion beam. The irradiation dose and the irradiation point of each irradiation spot 42 and the excitation amount of the scanning magnet power supply 61 corresponding thereto are in accordance with the prescribed treatment planning, and contents thereof are transmitted from the treatment planning system. 67 to the central control system 65 before the treatment is started and are stored in the memory in the irradiation control system 64. According to the contents thereof, the irradiation control system 64 defines the excitation pattern of the scanning magnet power supply 61, and the central control system 65 transmits the energy corresponding to the depth, which is obtained by dividing the target volume 41 into layers in the depth direction, to the accelerator control system 66 or a transport control system 68 and performs the operation with the corresponding energy. When the irradiation of one layer of the target volume 41 is completed, an energy switching instruction is transmitted so as to perform the operation with energy corresponding to another layer. By repetition of these operations, the irradiation of the entire target volume 41 is completed.

On the other hand, in the raster scanning method, the beam extraction is continued without stopping even when the irradiation point of the ion beam is moved from a certain lattice point to the next lattice point. That is, while the same slice is being scanned, the beam extraction is continued without interruption.

Therefore, when the irradiation dose of the ion beam irradiated to one spot 42 of the plurality of irradiation spots 42 reaches the target dose, the irradiation control system 64 controls the excitation current of the scanning magnets 51A and 51B to scan the ion beam, and changes the irradiation point to the next irradiation spot 42. In the meantime, the irradiation control system 64 does not stop the extraction of the ion beam from the ion beam generator 200, but controls the excitation current of the scanning magnets 51A and 51B in a state where the beam is extracted to scan the ion beam and controls so as to change the irradiation point to the next irradiation spot 42.

Details of the raster scanning method will be described in more detail below with reference to FIG. 5. A time chart illustrated in FIG. 5 shows the operation while a certain layer in the target volume 41 illustrated in FIG. 3 according to the present embodiment is irradiated.

In FIG. 5, a horizontal axis indicates a time t. FIG. 5(a) indicates the progression of the irradiation spot 42, and each of sections S1, S2, S3, and S4 indicates an irradiation section to each of the irradiation spots 42.

A vertical axis in FIG. 5 (b) represents an ion beam current that is extracted from the ion beam generator 200 and is injected to the irradiation apparatus 500 through the beam transport system 300. In the raster scanning method, since the transient response accompanying the beam OFF occurs only at the end of the slice, the influence due to the beam-off response delay is limited as compared with the discrete spot scanning method.

A vertical axis in FIG. 5(c) represents an integrated value of the measured dose of the dose monitor 53A and the irradiation dose detector 53B in the irradiation apparatus 500.

A vertical axis in FIG. 5(d) represents an excitation current of the scanning magnet power supply 61. At the same time that the integrated amount of irradiation illustrated in FIG. 5(c) reaches the planned dose prescribed in advance for each spot, it is determined that the irradiation of the irradiation spot 42 is completed, and the movement to the next irradiation spot is started. Therefore, the irradiation to the next irradiation spot 42 is first performed during the change of the excitation amount of the scanning magnet, and the change of the excitation amount of the scanning magnets 51A and 51B is stopped until the integrated amount of irradiation reaches the planned value after the change of the excitation amount is finished, and an operation of changing the excitation current of the scanning magnets 51A and 51B for shifting to the next spot at the same time that the dose reaches the planned value is repeated. Then, the ion beam continues to be irradiated during the operation.

A vertical axis in FIG. 5(e) represents a measurement state of the beam position monitor 52A and the beam position detector 52B at each irradiation spot 42, and a beam position at each irradiation spot 42 is measured by the beam position monitor 52A and the beam position detector 52B in the section M1 until the dose during the scanning and the scanning stop reaches the prescribed value, as described above.

After completion of the signal collection of the beam position detector illustrated in FIG. 5(e), the irradiation control system 64 calculates the beam position and a width (standard deviation) based on the collected signal and compares with a tolerance set previously in the memory of irradiation control system 64, thereby determining whether the beam position/width value is within a desired error range.

In FIG. 5, the start of the irradiation at the section S2 in the irradiation spot 42 is the timing after the end of the irradiation at the section S1 in the irradiation spot 42. The flow after the completion at the section S1 in the irradiation spot 42 is also repeated after the irradiation at the section S2 in the irradiation spot 42, and two-dimensional scanning as illustrated in FIG. 3 proceeds.

As in the repetition of the series of operations illustrated in FIGS. 4(a) to (f), even when the series of operations illustrated in FIGS. 5(a) to (e) are repeated, the layer in the depth direction of the target volume 41 illustrated in FIG. 3 is irradiated with the ion beam according to the treatment planning.

In such a raster scanning method, the irradiation of the beam is stopped in a case where a space between the irradiation spots 42 becomes large while irradiating one layer of the target volume 41 illustrated in FIG. 3 and the dose to be irradiated therebetween cannot be ignored, in a case of irradiating a certain layer illustrated in FIG. 3 to change it to another depth layer, that is, to change the energy of the ion beam to be injected into the irradiation apparatus 500, or in a case where an unacceptable beam stop factor occurs.

Regardless of the irradiation control method, the irradiation control system. 64 reads the signal obtained from the beam position monitor 52A and the beam position detector 52B from the inside of the irradiation control system 64, and then the irradiation control system 64 calculates the beam position and width and determines whether the calculation value of the ion beam position/width deviates from the tolerance. Then, when the calculation value of the ion beam position/width deviates from the tolerance, the irradiation control system outputs an interlock signal to the accelerator control system 66 via the central control system 65, and stops the extraction of the ion beam from the ion beam generator 200.

In the particle therapy system according to the present embodiment, whether to perform any one irradiation method of the raster scanning method and the discrete spot scanning method can be previously selected depending on the target volume 41 of the patient 4 to be irradiated, and both the irradiation methods of the raster scanning method and the discrete spot scanning method are configured to be performed by one common ion beam generator 200, one common beam transport system 300, one common irradiation apparatus 500, and the control system 600 in which many units are united.

The configuration for that will be described below.

The control system 600 is a system for controlling respective apparatuses included in the synchrotron 20, the beam transport system 300 and the irradiation apparatus 500, and includes the accelerator control system 66, the irradiation control system 64, the central control system 65, the transport control system 68, and the treatment planning system 67.

The treatment planning system 67 is a system for preparing a plan to irradiate an ion beam, and prepares a treatment planning by treating and selecting with any one of a raster scanning method and a discrete spot scanning method, based on information on the target volume 41 of the patient 4 to be irradiated. The treatment planning system 67 outputs the prepared treatment planning to the central control system 65.

The central control system 65 outputs a control signal to each of the control systems, which are the accelerator control system 66, the irradiation control system 64, and the transport control system 68, such that irradiation control on the target volume 41 of the patient 4 is performed with the irradiation method of any one of the raster scanning method and the discrete spot scanning method based on the input treatment planning. The central control system 65 further includes a display unit 65*a* displaying which irradiation method of either the raster scanning method or the discrete spot scanning method is selected.

The accelerator control system 66 includes a common control unit 66*a* used in any of the irradiation methods, a non-stop control unit 66*b* used only in the raster scanning method, and a stop control unit 66*c* used only in the discrete spot scanning method, and each apparatus in the ion beam generator 200 such as the synchrotron 20 is controlled by the accelerator control system 66. In the accelerator control system 66, based on the control signal from the central control system 65, control is performed by the common control unit 66*a* and the non-stop control unit 66*b* in a case where irradiation is performed with the raster scanning method, and control is performed by the common control unit 66*a* and the stop control unit 66*c* in a case where irradiation is performed with the discrete spot scanning method. For example, the common control unit 66*a* is a common control parameter set between the discrete spot scanning method and the raster scanning method, and is used to control the preaccelerator 21, the bending magnet 22, and the radiofrequency acceleration system 23 which are common in both methods for control when particles are injected from the preaccelerator 21 and the particles are accelerated in the synchrotron 20. The non-stop control unit 66*b* is a control parameter set used only in the raster scanning method, and is used for controlling the extraction apparatus 24 and the extraction switch 25. The stop control unit 66*c* is a control parameter set used only in the discrete spot scanning method, and is used for controlling the extraction apparatus 24 and the extraction switch 25. Apparatuses such as extraction electromagnets and beam extraction control that are common in both methods need to achieve beam current response speed that satisfies the requirements of the discrete spot scanning method.

In addition, in the accelerator control system 66, the stop control unit 66*c* corresponding to the discrete spot scanning method is used for irradiation with the raster scanning method, and it is possible to perform the control with both methods by one common control unit. In this case, at the time of irradiation with the raster scanning method, normally the stop control unit 66*c* transmits a beam OFF signal when the irradiation dose reaches a specified value, and it is controlled to maintain the beam in ON state until finishing the slice.

The irradiation control system 64 includes a common control unit 64*a* used in any of the irradiation methods, a non-stop control unit 64*b* used only in the raster scanning method, and a stop control unit 64*c* used only in the discrete spot scanning method, and controls each apparatus in the irradiation apparatus 500. In the irradiation control system 64, based on the control signal from the central control system 65, control is performed by the common control unit 64*a* and the non-stop control unit 64*b* in a case where irradiation is performed with the raster scanning method, and control is performed by the common control unit 64*a* and the stop control unit 64*c* in a case where irradiation is performed with the discrete spot scanning method. For example, the common control unit 64*a* is a common control parameter set between the discrete spot scanning method and the raster scanning method, and controls power supply of the scanning magnet power supply 61 common to both methods. The non-stop control unit 64*b* is a control parameter set used only in the raster scanning method, and the stop control unit 64*c* is a control parameter set used only in the discrete spot scanning method and controls the beam position detector 52B or the irradiation dose detector 53B which are different in timing or control method in the both methods, for example.

The transport control system 68 controls each apparatus such as the bending magnet 31 in the beam transport system 300.

Effects of the present embodiment will be described below.

The particle therapy system according to the present embodiment can obtain various advantages that irradiation can be realized using both types of the raster scanning method and the discrete spot scanning method having the same basic configuration with one irradiation apparatus 500, an appropriate method depending on the irradiation object can be selected, both improvement of irradiation accuracy and high dose rate can be achieved, and irradiation can be performed at a short time. For example, in a case of irradiating in synchronization with movement while confirming the movement of the target volume such as childhood cancer with X-rays, the irradiation is performed by the discrete spot scanning method with high accuracy. In a case of prostate cancer in which movement of the target volume is small, an irradiation time can be shortened by continuously striking with the raster scanning method for a long period. Since both irradiation methods can be realized with a single system, there are also advantages that the system becomes inexpensive and the size of the treatment system can be reduced.

It is to be noted that although the case of using the extraction apparatus 24 including the extraction radiofrequency electrode for extraction as the beam extraction apparatus has been described by way of example, the beam extraction apparatus is not limited to the extraction apparatus 24, and may use a quadrupole magnet for extraction, a betatron core, or the like.

Second Embodiment

A particle therapy system according to a second embodiment of the present invention will be described with reference to FIG. 6. The same reference numerals are given to the same configurations as those in FIGS. 1 to 5, and a description thereof will not be presented. This is also applied to the following embodiments. FIG. 6 is a schematic diagram illustrating an overall configuration of the particle therapy system according to the second embodiment.

In a particle therapy system 101 according to the present embodiment, whether to perform any one irradiation method of the raster scanning method and the discrete spot scanning method can also be selected based on the previous selection depending on the target volume 41 of the patient 4 to be irradiated, and either of the irradiation methods of the raster scanning method and the discrete spot scanning method is configured to be capable of being performed by one irradiation apparatus 500.

As illustrated in FIG. 6, a treatment planning system 67A according to the present embodiment includes a selection unit 67a1 that allows an operator to select any irradiation method of the raster scanning method and the discrete spot scanning method for treatment at the time of preparing the treatment planning, and prepares a treatment planning with the irradiation method selected by the selection unit 67a1. The treatment planning system 67A outputs the prepared treatment planning to the central control system 65.

The configuration and operation of components other than the treatment planning system 67A are substantially the same as those of the particle therapy system according to the first embodiment described above, and the details are not be presented.

In the particle therapy system according to the second embodiment of the present invention, it is possible to prepare the treatment planning with excellent balance between the dose distribution accuracy and the irradiation time by allowing the operator to select from two spot scanning methods at the time of treatment planning or to change the method. Particularly, in the raster scanning method, since the dose is also applied between the irradiation spots, the overall dose distribution largely depends not on the position of the irradiation spot but also on the scanning path and the present or absence of moving object tracking control. It is therefore desirable for the treatment planning system 67A to compare and confirm the dose distribution when each spot scanning method is selected at the treatment planning stage for the purpose of improvement of the dose distribution accuracy and from the calculation capability, and the treatment planning system 67A has a large effect of providing a function capable of selecting two spot scanning methods.

Furthermore, a case is also considered which combines the treatment planning system capable of selecting two spot scanning methods with the particle therapy system capable of performing two spot scanning methods with a single common irradiation apparatus. This is because it becomes unnecessary to successively correct the differences in characteristics and performances due to the state of the nozzle, the transport system, and the accelerator which are necessary for another apparatus or the individual difference at the time of changing two spot scanning methods, whereby dose distribution calculation efficiency is improved, the dose distribution is improved, or the time loss required for switching is reduced.

Third Embodiment

A particle therapy system according to a third embodiment of the present invention will be described with reference to FIG. 7. FIG. 7 is a schematic diagram illustrating an overall configuration of the particle therapy system according to the third embodiment.

In a particle therapy system 102 according to the present embodiment, whether to perform any one irradiation method of the raster scanning method and the discrete spot scanning method can also be selected based on the previous selection depending on the target volume 41 of the patient 4 to be irradiated, and either of the irradiation methods of the raster scanning method and the discrete spot scanning method is configured to be capable of being performed by one irradiation apparatus 500.

As illustrated in FIG. 7, a central control system 65B of the particle therapy system 102 according to the present embodiment includes an input unit 65b1 that receives input of information on the target volume 41 of the patient 4 to be irradiated from a treatment planning system 67B outside the system 102. The central control system 65B analyzes the information on the target volume 41 of the patient 4 input to the input unit 65b1, determines whether the irradiation control is performed on the target volume 41 of the patient 4 by any irradiation method of the raster scanning method and the discrete spot scanning method, and outputs the control signal to the respective control system of the accelerator control system 66, the irradiation control system 64, and the transport control system 68.

The configuration and operation of components other than the central control system 65B and the treatment planning system 67B are substantially the same as those of the particle therapy system according to the first embodiment described above, and the details are not be presented.

The particle therapy system according to the third embodiment of the present invention can be obtained substantially the same effect as that of the particle therapy system according to the first embodiment described above.

It should be noted that the input unit 65b1 of the central control system 65B is not limited to the aspect in which the input of the information on the target volume 41 of the patient 4 to be irradiated is received from the treatment planning system 67B outside the system 102, and may include an aspect of inputting information on selection by the operator at the time of preparing the treatment planning or an aspect of inputting information on selection by the operator other than the preparation timing of the treatment planning.

In addition, when the particle therapy system 102, the central control system 65, or the treatment planning system 67 selects either the raster scanning method or the discrete spot scanning method, the dose distribution accuracy, the obtained dose rate, the treatment time is calculated, the irradiation method close to numerical values based on parameters described in the table stored in advance is selected in addition thereto, and these items may be displayed on a display unit 65a. In that case, either the raster scanning method or the discrete spot scanning method is then selected based on the display by the input of the operator to the central control system 65B.

Fourth Embodiment

A particle therapy system according to a fourth embodiment of the present invention will be described with reference to FIGS. 8 and 9. FIG. 8 is a schematic diagram illustrating an overall configuration of the particle therapy system according to the fourth embodiment.

In the particle therapy system, the confirmation of the position of the target volume is important for forming the dose distribution conformal to target shape. Particularly, in order to improve the dose distribution accuracy on the target volume moving with the movement of the body such as respiration, there is a method of irradiating the ion beam in synchronization with the movement of the target volume accompanying the movement or the respiration of the patient by measuring the movement of the chest according to the movement of the body surface or measuring the target volume, a marker in the vicinity of the target volume, or a region having a high density with an MRI, an X-ray, or other radioactive rays.

In the raster scanning method, since the ion beam is continuously irradiated, there is one aspect in which the response to respiration synchronization irradiation, which needs to turn on/off of the ion beam irregularly, is not easy. In addition, when the X-ray is exposed for tracking a moving object during the particle beam irradiation in the raster scanning method, there is a problem that timing suitable for exposure to the X-ray in which the particle beam irradiation is stopped does not exist. Further, if X-ray exposure for tracking the moving object is performed regardless of the particle beam irradiation, problems may arise in measurement accuracy of irradiation dose and accuracy of identification of the target volume. The present embodiment is to provide the particle therapy system for achieving both improvement of dose distribution accuracy and high dose rate by appropriately using the irradiation method with the same apparatus even when irradiating the target volume moving with the movement of the body such as respiration.

As illustrated in FIG. 8, the particle therapy system 103 according to the present embodiment includes a fluoroscopic X-ray imaging apparatus 510.

The fluoroscopic X-ray imaging apparatus 510 includes two X-ray generators for generating an imaging X-ray capable of pulse irradiation and two X-ray image receivers for detecting the generated X-ray. The irradiation timing of the X-ray generator is controlled, and each apparatus is installed in the treatment room 400 so that the imaging can be performed in biaxial directions. That is, the X-ray generator and the X-ray image receiver are disposed so as to face each other with a region where the patient is placed, and the X-ray image receiver is installed on the beam delivery system. Two line segments connecting the X-ray generator and the X-ray image receiver facing each other are installed so as to intersect with each other in the region where the target volume 41 of the patient 4 is placed.

A relation between movement detection of the target volume 41 and beam irradiation will be described with reference to FIG. 9. FIG. 9(a) indicates a signal that detects the movement of the target volume 41, and sets a threshold for guaranteeing that the target volume 41 is at a desired position or within a certain range from the desired position with respect to the signal. The beam is irradiated only when there is a position detection signal of the target volume 41 within the threshold. In this case, the timing at which the irradiation apparatus 500 according to the present embodiment can irradiate is as illustrated in FIG. 9(b), and since the signal is movement accompanying the movement of the patient, the timing can be irregular.

As described above, when the method of detecting the movement of the target volume 41 and irradiating in only the case where the movement amount is within the desired range is adopted, the particle beam irradiation is difficult with the raster scanning method, but can easily be performed with the discrete spot scanning method.

Therefore, the information on the target volume 41 of the patient 4 to be irradiated includes information on whether the movement of the target volume 41 is detected, and the treatment planning system 67C selects, based on the information, any one of irradiation methods of the raster scanning method and the discrete spot scanning method used for treatment of the target volume 41 of the patient 4 to be irradiated, and prepares treatment planning. For example, the discrete spot scanning method is basically selected when the movement of the target volume 41 is detected, and the raster scanning method is selected in other cases.

The treatment planning system 67C outputs the prepared treatment planning to the central control system 65, and the central control system 65 outputs control signals to control systems of the accelerator control system 66, the irradiation control system 64, and the transport control system 68 such that the irradiation control is performed on the target volume 41 of the patient 4 by any one of irradiation methods of the raster scanning method and the discrete spot scanning method, based on the information on the target volume 41 of the patient 4 input from the treatment planning system 67C. In the present embodiment, a fluoroscopic X-ray image is acquired by the fluoroscopic X-ray imaging apparatus 510 when the ion beam is irradiated onto the target volume 41 in the irradiation control system 64, and irradiation control of the particle beam is performed based on the acquired fluoroscopic X-ray image.

It should be noted that configurations other than those described above are substantially the same as those of the particle therapy system according to the first embodiment described above, and their operations are basically the same, so the details are not be presented.

The particle therapy system according to the fourth embodiment of the present invention can be obtained substantially the same effect as that of the particle therapy system according to the first embodiment described above.

Particularly, according to the particle therapy system of the present embodiment, even when the particle beam is irradiated onto the target volume moving accompanying the movement of the body such as respiration, the irradiation apparatus of both types of spot scanning is not necessary to be realized by a separate treatment room, a separate irradiation apparatus, or a plurality of switching nozzles, and it is possible to improve both the dose distribution accuracy and the high dose rate without increasing costs and enlarging the installation area.

Although the fluoroscopic X-ray imaging apparatus 510 is used as a unit for detecting the movement of the target volume 41 of the patient 4, it is considered that the movement detection unit includes, for example, a method of monitoring the movement of the body surface for detecting respiratory movement and a method of monitoring the flow of expiration and inspiration accompanying the respiration of the patient at the mouth of the patient without being limited to the fluoroscopic X-ray imaging apparatus 510.

In addition, the fluoroscopic X-ray imaging apparatus 510 may be disposed to perform imaging from one axis direction, and the X-ray generator and the X-ray image receiver may be disposed in a reverse manner.

<Others>

The present invention is not intended to be limited to the embodiments described above, and includes various modifications. For example, the embodiments are described in detail in order to better illustrate the present invention and are not intended to limit the present invention always to those inclusive of full configuration as described above. In addition, the configuration of a certain embodiment can partially be replaced by the configuration of another embodiment, or the configuration of a certain embodiment can be added with the configuration of another embodiment. Also, the configuration of respective embodiments can partially be removed, or added with or replaced by another configuration.

For example, a unit for selecting either of the raster scanning method and the discrete spot scanning method depending on the irradiation object may be provided in the process from the reception of the patient 4 to the treatment, and the ion beam may be irradiated onto the target volume 41 with one irradiation apparatus 500 using the irradiation method selected by such a selection unit.

REFERENCE SIGNS LIST

4: patient
20: synchrotron
21: preaccelerator
22: bending magnet
23: radiofrequency acceleration system
24: extraction apparatus
25: extraction switch
26: radiofrequency power supply
31: bending magnet
41: target volume
42: irradiation spot
43: path
51A: X-direction scanning magnet
51B: Y-direction scanning magnet
52A: beam position monitor
52B: beam position detector
53A: dose monitor
53B: irradiation dose detector
61: scanning magnet power supply
62: power supply control system
64: irradiation control system
64a: common control unit
64b: non-stop control unit
64c: stop control unit
65, 65B: central control system
65a: display unit
65b1: input unit
66: accelerator control system
66a: common control unit
66b: non-stop control unit
66c: stop control unit
67, 67A, 67B, 67C: treatment planning system
67a1: selection unit
68: transport control system
100, 101, 102, 103: particle therapy system
200: ion beam generator
300: beam transport system
400: treatment room
500: irradiation apparatus
510: fluoroscopic X-ray imaging apparatus
600: control system

The invention claimed is:

1. A particle therapy system that divides an irradiation object into a plurality of dose sections and sequentially irradiates the plurality of dose sections with a particle beam, comprising:
   an accelerator that accelerates the particle beam;
   an irradiation apparatus that irradiates a target with the particle beam accelerated by the accelerator;
   a fluoroscopic X-ray imaging apparatus; and
   a control system that controls the accelerator, the irradiation apparatus and the fluoroscopic X-ray imaging apparatus,
   wherein the control system is configured to control the accelerator and the irradiation apparatus to perform both a first irradiation method in which irradiation of the particle beam is not stopped when moving to a next dose section of the plurality of dose section and a second irradiation method in which irradiation of the particle beam is stopped when moving to the next dose section of the plurality of dose section, and
   wherein the control system is configured to control the fluoroscopic X-ray imaging apparatus to acquire a fluoroscopic X-ray image at the time of irradiation, and, when irradiation control of the particle beam is performed based on the acquired fluoroscopic X-ray image, the irradiation is performed by the second irradiation method in which the irradiation of the particle beam is stopped when moving to the next dose section.

2. The particle therapy system according to claim 1, further comprising:
   a planning apparatus that prepares a plan to irradiate the particle beam, wherein
   the planning apparatus is configured to prepare treatment planning, based on information on the irradiation object, by any one of the first irradiation method and the second irradiation method, and the control system is configured to control the irradiation apparatus to perform, based on the prepared treatment planning, any one of the first irradiation method and the second irradiation method.

3. The particle therapy system according to claim 1, further comprising:
   a planning apparatus that prepares a plan to irradiate the particle beam, wherein
   the planning apparatus is configured to prepare treatment planning, based on selection of an operator, by with any one of the first irradiation method and the second irradiation method, and the control system is configured to control the irradiation apparatus to perform, based on the treatment planning, any one of the first irradiation method and the second irradiation method.

4. The particle therapy system according to claim 1, further comprising:
   an input unit that receives information on the irradiation object,
   wherein, based on the information on the irradiation object input to the input unit, any one of the first irradiation method and the second irradiation method is selected.

5. The particle therapy system according to claim 1, wherein
   any one of the first irradiation method and the second irradiation method is capable of being selected in advance depending on the irradiation object.

6. The particle therapy system according to claim 1, further comprising:
a display unit that displays which one of the first irradiation method and the second irradiation method is selected.

7. The particle therapy system according to claim 1, wherein
the control system includes an irradiation control system that controls the irradiation apparatus, and
the irradiation control system includes a common control unit used in any of the first irradiation method and the second irradiation method, a non-stop control unit used only in the first irradiation method, and a stop control unit used only in the second irradiation method.

8. A particle therapy system comprising:
an accelerator that accelerates a particle beam;
an irradiation apparatus that irradiates a target with the particle beam accelerated by the accelerator;
a fluoroscopic X-ray imaging apparatus;
a control system that controls the accelerator, the irradiation apparatus and the fluoroscopic X-ray imaging apparatus; and
an input unit that receives information on whether to irradiate the particle beam with any one of a raster scanning method and a discrete spot scanning method,
wherein the control system is configured to control the fluoroscopic X-ray imaging apparatus to acquire a fluoroscopic X-ray image at the time of irradiation, and, when irradiation control of the particle beam is performed based on the acquired fluoroscopic X-ray image, the irradiation is performed by the discrete spot scanning method in which the irradiation of the particle beam is stopped when moving to a next dose section of a plurality of dose sections of an irradiation object.

9. The particle therapy system according to claim 8, wherein
the irradiation according to raster scanning method and the discrete spot scanning method are each performed via a common nozzle.

10. The particle therapy system according to claim 8, wherein
extraction control of the accelerator in the irradiation according to the raster scanning method and the discrete spot scanning method are each performed via a common accelerator control system.

* * * * *